(12) United States Patent
Gerwen et al.

(10) Patent No.: US 6,440,662 B1
(45) Date of Patent: Aug. 27, 2002

US006440662B1

(54) IMPEDIMETRIC DETECTION SYSTEM AND METHOD OF PRODUCTION THEREOF

(75) Inventors: Peter Van Gerwen, Opwijk; Kris Baert, Heverlee; Rudi Rossau, Ekeren, all of (BE)

(73) Assignee: Innogenetics N.V., Ghent (BE)

( * ) Notice: Subject to any disclaimer, the term of this patent is extended or adjusted under 35 U.S.C. 154(b) by 0 days.

(21) Appl. No.: 09/077,480

(22) PCT Filed: Nov. 29, 1996

(86) PCT No.: PCT/EP96/05290

§ 371 (c)(1),
(2), (4) Date: May 3, 1999

(87) PCT Pub. No.: WO97/21094

PCT Pub. Date: Jun. 12, 1997

(51) Int. Cl.[7] .......................... C12Q 1/68; G01N 27/26; G01F 1/64; B05D 5/12
(52) U.S. Cl. .......................... 435/6; 204/412; 205/775; 427/126.3; 427/126.5
(58) Field of Search .......................... 435/6; 427/126.3, 427/126.5; 422/68.1, 50; 324/76.11; 205/775; 204/412, 413

(56) References Cited

U.S. PATENT DOCUMENTS 5,494,701 A * 2/1996 Clough et al. ........... 427/126.3

FOREIGN PATENT DOCUMENTS

| EP | 213825 | 3/1987 |
|---|---|---|
| EP | 241771 | 10/1987 |
| EP | 543550 | 5/1993 |
| GB | 2137361 | 10/1984 |
| GB | 2210462 | 6/1989 |
| GB | 2215846 | 9/1989 |
| WO | 93/22678 | 11/1993 |

OTHER PUBLICATIONS

Connolly "Bioelectronic interfacing: mirco–and nanofabrication techniques for generating predetermined molecular arrays; for use in biosensors, biochip, switching device, bioelectronics, etc.: review," (1994), Trends Biotechnol. vol. 12, No. 4 pp. 123–127.*

* cited by examiner

*Primary Examiner*—John S. Brusca
*Assistant Examiner*—Young Kim
(74) *Attorney, Agent, or Firm*—Knobbe, Martens, Olson & Bear LLP

(57) ABSTRACT

A sensor for identifying molecular structures within a sample solution is disclosed. The sensor comprises an insulating layer with a plurality of interspaced channels therein having essentially the same direction. The channels furthermore have submicron dimensions. A method of fabricating a sensor for identifying molecular structures within a sample solution is also disclosed.

40 Claims, 10 Drawing Sheets

IMPEDIMETRIC DETECTION SYSTEM AND METHOD OF PRODUCTION THEREOF

This application is a U.S. National Phase application of PCT application no. PCT/EP96/05290, filed Nov. 29, 1996.

The present invention relates to an improved sensor for electronically detecting a binding reaction between molecular structures or a pair of chemical substances, such as oligonucleotides, antigens, enzymes, peptides, antibodies, DNA and RNA fragments.

The present invention further provides a new production method for this improved sensor.

Techniques and sensors for detecting molecular structures and specific substances such as enzywes, peptides, oligonucleotides, antigens antibodies, DNA and RNA fragments in a solution sample are known in the art. In a specific class of sensors, use is made of the principle of measuring the impedance between two electrodes. The absence or presence of DNA-molecules or antibodies or antigens between the electrodes affects the permittivity and/or the conductivity between the electrodes. Various techniques were proposed to measure the presence and/or concentration of a given analyte in a sample solution by using a binding substance element having specific affinity for the analyte. Such specific binding reactions occur e.g. between enzymes and their substrates, antibodies and antigens, between DNA-DNA, between RNA-DNA, or other molecular structures.

Stoner et al in "Adsorption of blood proteins on metals using capacitance techniques", *J. Phys. Chem.*, 74, Mar. 5, 1970, describe a differential capacity measurement for evaluation of protein adsorption on metalic electrodes.

Arwin et al. in U.S. Pat. No. 4,072,576, use an adsorbed polypeptide substrate and establish a capacitive method for the measurement of enzymatic activity and the immunological interaction assay.

Giaever in U.S. Pat. No. 4,054,646, teaches an electrical method that measures the presence of antibodies in a solution, by coating a metallic substrate with an antigen. After the incubation of the electrodes with the sample solution, he measures capacitively the thickness of the molecular sheet, i.e. he distinguishes between mono- and bimolecular layer, by using a mercury drop as a second electrode.

Newman in Patent application WO87/03095 discloses a capacitive sensor for chemical analysis and measurement. Said sensor can be used to detect a broad range of analytes including bacteria, viruses, antibodies, antigens, enzyme substrates and hormones. A thin insulating layer is coated on the surface of conductors and a substrate to form an open capacitor. A biospecific binding agent is immobilized on the surface of the insulating layer between the conductors. The dielectric constant of the biospecific binding agent is altered by binding of the analyte being detected with the biospecific binding agent. A similar sensing principle is disclosed in U.S. Pat. No. 5,114,674.

Battailard et al, 1988, *Anal.Chem.*, 60, 2374–2379 and more recently, Klein et al, 1995, *Sensors and Actuators*, B 2627, pp. 474–476, show that a metal-semiconductor-insulator device can be used in a similar way as a MIS (metal-insulator-semiconductor) capacitor. The device is immersed in a solution together with a second, reference electrode. By measuring the ac capacity between the metallic layer of the device and the reference electrode, when dc biasing voltages are simultaneously applied, the fiat band voltage of the system is in fact measured in a similar way as in the case of a MIS capacitor. It was proven that the flat band voltage can be modulated by species adsorbed at the insolation-liquid interface. On this principle work the ISFET, ion-sensitive-field-effect-transistor and GENFET, gene-sensitive-field-effect-transistor.

U.S. Pat. No. 4,219,335, issued to Richard Ebersole discusses the use of immune reagents labeled with reactance tags. These tags can be detected ellectrically since they alter the dielectric, conductive or magnetic properties of the test surface.

Simlarly, EP 0 241 771, issued to S. J. Mroczkowski, teaches the detection of metal labeled antibodies by conductometric measurements. When antigens are immobilised inbetween two electrodes, the specific interaction with a metal-labeled antibody is measured by means of resistance decrease of the interelectrode medium.

M. Malmros in U.S. Pat. No. 4,334,880 describes conductivity variation of a semiconductive polymeric layer inbetween two planar electrodes. The said polymer incorporates, in a way or another, certain molecules able to recognize specific analytes. The recognition process induces conductivity changes of the polymeric layer.

Further variations on this central idea of impedimetric sensing appear in the art, EP 0 543 550, EP 0241 771, U.S. Pat. No. 4,453,126, GB 2,137,361, U.S. Pat. No. 3,999,122. Essentially in an impedimetric sensor, certain molecules are immobilised on the top, in between or both on the top and in between a pair of electrodes. Said molecules 'recognise' a specific analyte when exposed to a sample solution This recognition process eventually ends up, directly or indirectly, m conductivity and/or permitivity alteration of the space in the neighbourhood of the electrodes. Finally, by measuring the impedance between the two electrodes, a measure of the recognition process can be established.

The problem associated with the so called sensors as referred to above is that to have a good resolution, the immoblised layer should be perfectly homogenous and should not contain holes, which is hard to achieve.

With the advent of the microelectronic technology, there is a continuous effort to use it in order to develop microsensors. Sensors realised with microelectronic technology offer advantages such as low-cost production, increased reproducibility of the production process, uniformity, accurateness of detection, and flexibility in development. Such microelectronic sensors can comprise a multitude of individual test sites with reproducible, uniform electrical properties, whereby enhancing the detection sensitivity of the sensor. The test sites can be made with dimensions of the order of the dimensions of the molecules that have to be detected. The spatial limitations are the fabrication technology resolution and the sensitivity of the device which is dictated by the state of the art in instrumentation and the density of probes. A configuration can also be realised wherein the individual test sites can each yield a different type of signal according to the particular molecule which is to be detected in said test site.

Another important characteristic of the microelectronic technology is its planarity: the microelectrodes patterned this way are essentially flat elements. This feature is not a strong point in the impedimetric devices. In a planar impedimetric structure the electric field lines expand more above the device surface and out of the region of intrest in comparison to real 3-D structures. This is a major drawback especially when the region of interest is limited in space, i.e. it is an enzymatic or polymeric membrane or an adsorbed molecular layer at the surface of the structure. Any field line depassing this region of interest, introduces in the impedimetric response a shunting impedance which can be considered as noise for the measurement.

Still, depending on the electrodes geometry, i.e. dimensions and interspacing, a big majority of the total signal is enclosed in a certain region above the surface of the device as shown in FIG. 1. From the same figure one can deduce that miniaturisation, i.e. L decrease, is crucial in obtaining impedimetric planar structures that probe the space in the very close neighbourhood of the device. An illustration of the dimension down scaling was given by DeSilva et al DeSilva et al in 1995, *Biosensors & Bioelectronics*, 10, pp. 675–682 report a new biosensing structure that combines a covalent antibody immobilization technique with a simple impedance response method. The biosensor was fabricated by covalently binding anti-SEB antibodies onto an ultrathin, island-like, electrically continuous, Pt film deposited onto a silicon chip. They register an impedance decrease when the specific interaction with SEB takes place.

However, the reproducibility is low due to the somewhat random behavior of the fabrication process, i.e. the Pt deposition and the immobilisation procedure.

A true electrode patterning process is likely to insure a good reproducibility of the structures and to improve the control upon sensor behaviour. Devices with patterned features, said features having dimensions of hundreds of nanometers are expected to be highly sensitive to DNA fragments of 300 bases, i.e. Exhibiting a total molecular Tenth of about 180 nm, or to other large molecules like enzymes or antibodies (tens of nanometers diameter). This dimension range is usually achieved in two ways:

1. deep UV or X-ray lithography, techniques where about 100 nm features can be achieved with a fully optimised process.
2. electron-beampatterning, a tedious and very expensive technique where features of tens of nm can be obtained.

It is an aim of the present invention to provide an electrochemical sensor suitable for measuring the presence or absence of molecular structures.

It is another aim of the present invention to provide a method for fabricating as defined above.

It is yet another aim of the present invention to provide a method for detecting the presence of molecular structures in a sample.

The present invention relates to a new electrochemical sensor, based on the interference of an electrical field between electrodes with the analyte. The analyte to be tested is brought in the close neighbourhood of the structure by means of probes.

The present invention relates more particularly to a sensor for identifying molecular structures within a sample solution is disclosed. The sensor comprises an insulating layer with a plurality of interspaced channels therein having essentially the same direction. Said channels have a bottom and at least two opposite side-walls along said direction. The channels furthermore have submicron dimensions. A metal coating is applied on one of said two opposite side-walls of essentially each channel and on top of the insulating layer in between said channels thereby forming an impedimetric device with said sample solution within and between the channels. Optionally probes for binding to said molecular structures are already applied on said sensor. Said probes can be applied to either the insulating part of the channels (said bottom and the other side-wall of said channels), or to the surface of the electrodes or to both, the insulating part of the channels and the surface of the electrodes. Furthermore means are provided for applying a voltage on the metal coatings; as well as means for measuring the impedance in between the electrodes.

The term electrochemical sensor or shortly sensor according to the present invention refers to a device which transforms a (bio)chemical information into an electrical signal.

The present invention overcomes the problem of sensitivity compared to prior art sensors and methods. One important feature of this novel design is the high degree of miniaturisation. This is likely to reduce the noise of the structure and subsequently to increase its sensitivity. Another remarkable feature of the proposed sensor is its tridimensional geometry. This improves the electric field penetration in the area of interest with an eventual sensitivity increase. Said sensor has an interdigitated electrode structure which can be fabricated in a cheap way, even for large active areas.

The probes of the present invention are functionally defined as molecules able to react with another molecule to form a complex an/or induce a secondary reaction. It is by the way of example and not by way of limitation that probes can be enzymes, antibodies, antigens, peptides, DNA fragments, RNA fragments or oligonucleotides. Preferred probes according to the present invention are described in the following patents and patent applications held by one of the present applicants: EP 0 337 896; EP 0 345 375; EP 0 657 532; EP 0 419 355; EP 0 525 095; EP 0 494 317; EP 0489968; EP 0 644 202; WO 92/10514; EP 0 499 003; WO 92/11366; WO 92/16628; WO 92/19770; WO 93/08302; WO 93/18054; EP 0 561 087; WO 93/22437; WO 94/01554; EP 0 637 342; WO 94/13795; WO 94/18325; WO 94/21818; WO 94/25601; WO 95/12666; WO 95/17429; WO 95/33851; WO 96/00298; WO 96/04309; EP 0 721 505; WO 96/13590; WO 96/13608; WO 96/17065; and PCT applications filed under number 96/03091, 96/04146; as well as EP applications filed under Nos. 95870136.9, 96870006.2, 96870081.5, 96870053.4, 96870122.8 or 96870131.8. The contents of these patent (applications) and any other document referred to in this text are to be considered as incorporated by reference. The probes as well as the methods for making these probes are further discussed in the above-mentioned documents. It should be clear that these probes may be purified from a living source or may be made by any method of synthesis known in the art.

The targets to be detected in the sample or analyte can be any molecule present in a sample which binds or reacts with said probes. The targets can thus also include enzymes, antibodies, antigens, peptides, DNA fragments, RNA fragments, oligonucleotides or even whole cells. Depending on the type of targets and type of application, a specific type of recognition circuitry for processing the information related to target detection may be provided with or separately from the sensor.

The sample can be any biological sample (tissue or fluid) containing target molecules to be detected taken directly or after culturing (enrichment) from a healthy or an infected human being or animal More specifically these samples can include expectorations of any kind, blood, plasma, respiratory tract samples such as sputum, broncheolavages, skin tissue, biopsies, lymphoyte blood culture material, colonies, cerebrospinal fluid, brain tissue, urine, gastrointestinal tract, food, feed or environmental samples. Said samples may be prepared or ecxtracted by any method known in the art.

The sample may also be any preparation as described below (such as urea) or any other industrial product.

Alternatively, the sample to be tested may contain partially or fully purified target or analyte molecules, such as for instance amplified nucleotides, which have been solubilized in a solution. These solutions can be chosen from any type of solution known in the art which is suited for establishing a binding reaction between the specific probe and its target.

In the case of nucleotide detection, the sample material will include either genomic DNA or precursor RNA or amplified versions thereof The solution will be what is referred to a as hybridization solution. Upon hybridisation under what is referred to as "desired hybridisation characteristics according to the present invention", the probe (in this case an oligonucloetide) will only hybridize to the DNA or RNA from the specific organisms or molecules for which it was designed and not to the DNA or RNA from other organics or molecules such as closely related organisms or variant or mutated molecules which may also be present in a particular sample. In practice, this often implies that the intensity of the hybridization signal is at least two, three, four, five or even ten times stronger with the target DNA or RNA from the organisms from which the probes were designed, as compared to non-target sequences. Often it is desirable and achievable to detect nucleotide which perfectly match the probe nucleotide (implying that hybridization conditions are used in which one mismatch is detectable).

The hybridization conditions can be monitored relying upon several parameters, such as the nature and concentration of the components of the media or solutions, and the temperatures under which the hybrids are formed and washed. When modifications are introduced, be it either in the probes or the media, the temperatures at which the nucleotide probes can be used to obtain the required specificity should be changed according to known relationships, such as those described in Names and Higgins (eds.). Nucleic acid hybridization. A practical approach, IRL Press, Oxford, UK, 1985.

The probes may be applied to the sensor of the present invention in any manner known in the art, for instance immobilized by means of high resolution probe dispensing systems or even synthesized on the spot.

In another set-up also comprised within the scope of the present invention, the sample may be applied to the sensor and the probes may be added in solution to the ative test site area of the sensor to bring about a recognition which may be detected.

It should be stressed that the ability to simultaneously generate recognition results with a number of probes is an outstanding benefit of the sensors of the present invention.

In case of detection of antibodies present in a sample, the probe will be an antigen (e.g. a peptide or a polypeptide) or an anti-idiotype antibody known in the art. In case of detection antigens or polypeptides or peptides possibly present in a sample, the probe will be an antibody or a derivative thereof specifically binding to certain antigens, an antisense peptide specifically binding to certain peptides or polypeptides, a receptor or chemical molecule specifically binding to said polypeptide or peptide. The solution in which the possibly prepared or purified target material present in the sample may be dissolved, will be any solution which allows the binding between said binding molecules to occur. The conditions under which this formation may occur are well known in the art and are for instance further described in the above-mentioned patents and applications of the one of the applicants.

The present invention also relates to method of fabricating a sensor for identifying molecular structures within a sample substance. This method comprises the steps of forming a plurality of interspaced channels in a insulating layer, said channels having essentially the same direction, said channels having a bottom and at least two opposite side-walls along said direction; depositing a metal layer on said insulating layer while aligning said dielectric layer with respect to the metal deposition source such that the bottom of said channels and the side-walls of said canals along the deposition direction are shadowed and not covered by metal to thereby form an impedimetric device with said sample substance within and between the channels and eventually immobilising probes for binding to said molecular structures, said probes being applied to either the insulating part of the channels (said bottom and the other side-wall of said channels), or to the surface of the electrodes or to both, the insulating part of the channels and the surface of the electrodes.

The present invention represents an important tool in a wide field of applications and it is by the way of example and not byway of limitation suited for measuring specific interactions like the reaction between an enzyme and its substrate or the recognition reaction between an antibody and an antigen, between DNA-DNA, between RNA-DNA, or other molecular structures; in the study of the reaction kinetics of said specific interactions; for sequencing molecules such as peptides, enzymes, nucleotides, DNA, RNA and so on; for detecting genes mutations; for epidemiology and geno- or sero typing or for instance HLA and HCV; for drug susceptibility testing like the resistance against beta-lactamase and tetracycline in *Neisseria gonorrhoeae*, the detection of rifampicin resistant *Mycobacterium tuberculosis* strains or the detection of AZT-resistance in HIV; in screening and diagnosis[]viral diagnosis: like in the case of HIV, HCV, HBV, herpes and relatives, CMV, BPV or HTLV; bacterial diagnosis like in the case of sexually transmitted diseases, cerebral spinal fluid analysis, detection of different mycobacterial species, evaluation of anaerobic infections, otitis, respiratory tract, gastro-intestinal tract, periodontal pathogens, pathogenic fingi; genetic diseases, like cystic fibrosis, Alzheimer, detection of mitochondrial mutations, platelet antigens, drug receptors, risk factors for atherioscrerosis and coronary heart dieases, cancer, APOE, AChE, APOB, LDL and so on; in clinical analysis: like in the case of conductometric urea or creatinine quantitation.

The high sensor miniaturisation also allows the construction of integrated microdiagnostic devices capable of simultaneous detection of a multitude of parameters, i.e. multiparameter testing, and ultimately screening assays.

| | |
|---|---|
| BCB | Benzocyclobuteen |
| LPCVD | Low Pressure Chemical Vapour Deposition |
| PECVD | Plasma Enhanced Chemical Vapour Deposition |
| PMMA | polymethylmetacrylaat |
| PEEK | Poly(etherether)keton |
| PC | Polycarbonaat |
| PVE | Polyvinylethyleen |
| PEI | Polyethyleneimine |
| CMV | Cytomegalovirus |
| HPV | Human papilloma virus |
| HTLV | Human T-cell leukemia virus |
| APOE | Apolipoprotein E |
| APOB | Apolipoprotein B |
| AchE | Acetylcholinesterase |
| LDL | Low density lipoprotein |
| HLA | Human leukocyte antigen |
| HCV | Hepatitis C virus |
| HIV | Human immunodeficiency virus |
| HBV | Hepatitis B virus |
| LIGA | Lithographie, Galvanik Abformung |

BRIEF DESCRIPTION OF THE DRAWINGS

FIG. 6 illustrates the working principle of one of the possible embodiment of the sensor according to the present invention.

EXAMPLES AND DETAILED DESCRIPTION OF THE INVENTION

Preferred exemplary embodiments of the present invention will hereafter be described in conjunction with the appended drawings. It is to be understood that the examples given are only for the purpose of teaching of the invention, the spirit and scope of this patent application being limited only by the terms of the appended claims.

The sensor of the present invention comprises an insulating layer with metallic electrodes on the top. A submicron pattern is made in the insulating layer. The metal top layers are in a specific geometry thereby enhancing the detection sensitivity of the sensor. Said sensor can further comprise a base layer.

Figure 1A:
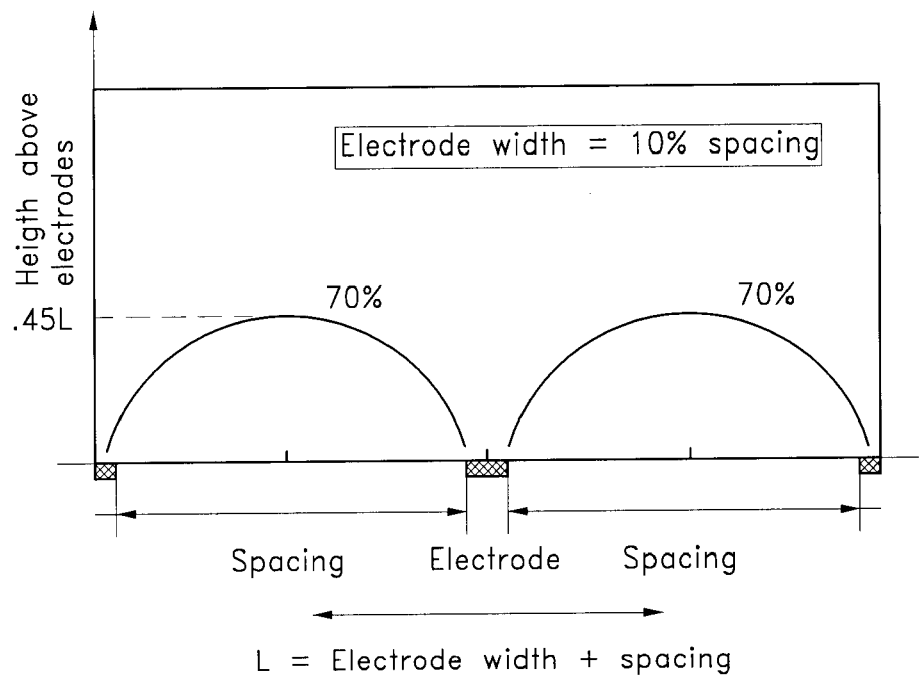
FIG. 1 is an illustration of the dependence of the electrical field penetration depth in the case of a planar structure with the electrodes geometry (different ratios of (electrode width)/(electrode interspacing)) and dimension, L.
Figure 1B:
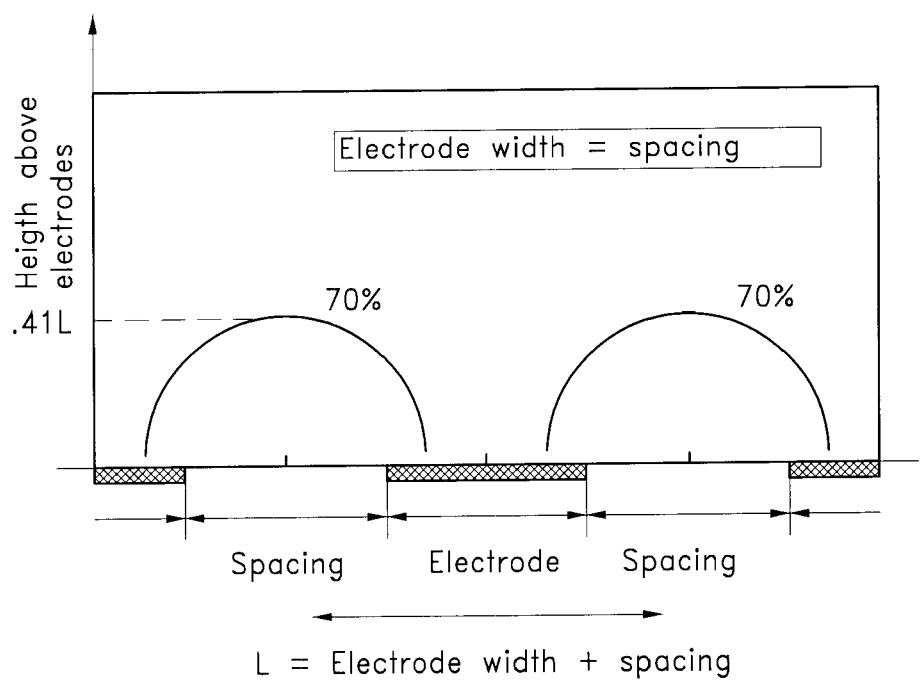
Figure 1C:
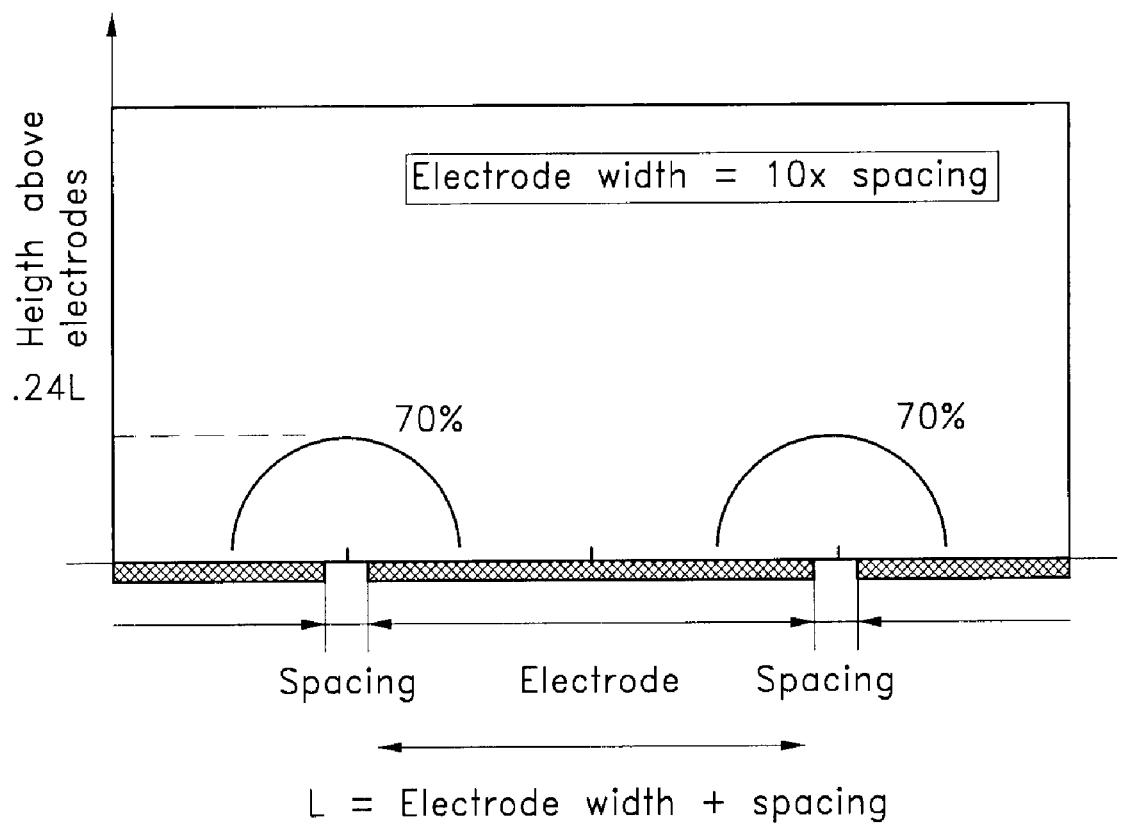
Figure 2:
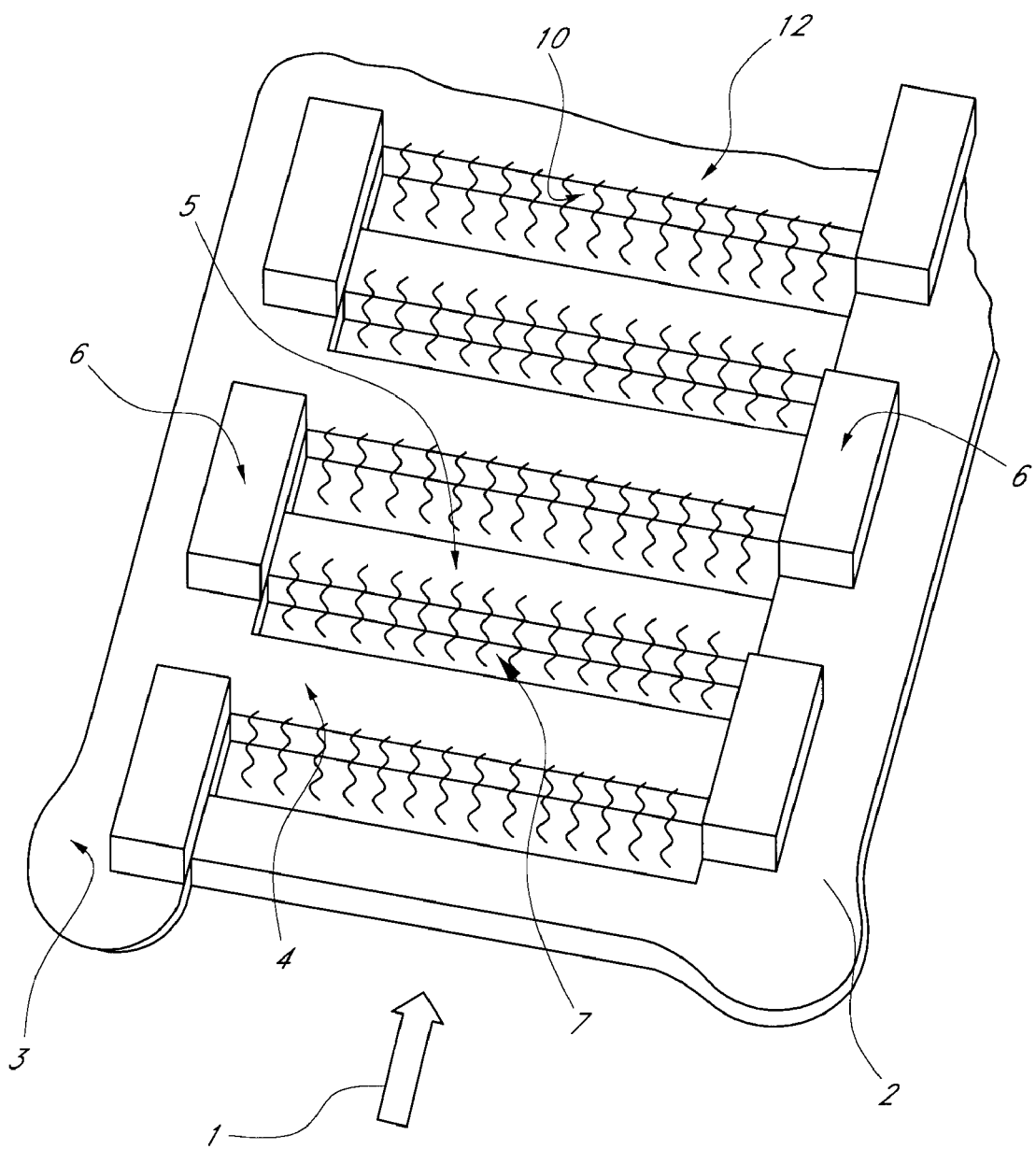
FIG. 2 is a schematic drawing of the active sensor test site area of an embodiment of a bioelectronic sensor according to the present invention. Numbering used in FIGS. 2–7 is as follows: (1) direction of evaporation or deposition of metal; (2) first bonding pad of one sensor; (3) second bonding pad of one sensor; (4) 'even' planes of electrode fingers; (5) 'odd' planes of electrode figures; (6) hills, blocking planes (4) from (5); (7) channels; (8) mask for separation of different sensors; (9) shaded arrays (shaded from metal deposition); (10) probes; (11) field lines of a sensor on which a voltage is applied; (12) to be detected molecules; (13) sacrificed electrodes in the separation step; (14) width of all interdigitated electrodes together of one sensor; (15) left side of devide with separate functions: electrodes; (16) right side of said device: area with probes.
Figure 3A:
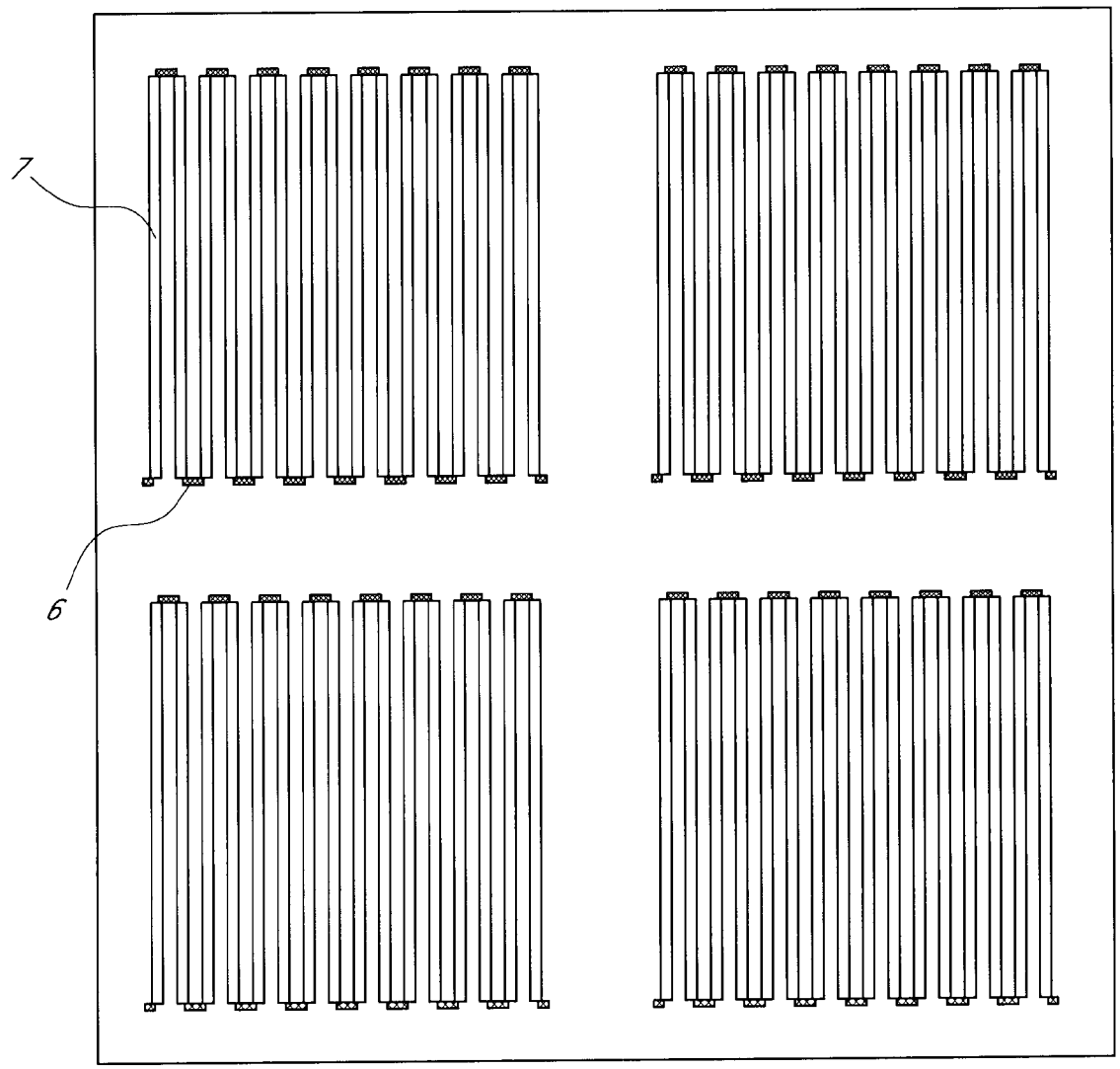
FIG. 3a is a schematic drawing, representing a base plate for making an array of 2×2 sensors (by way of example and not by way of limitation) according to an embodiment of the present invention.
Figure 3B:
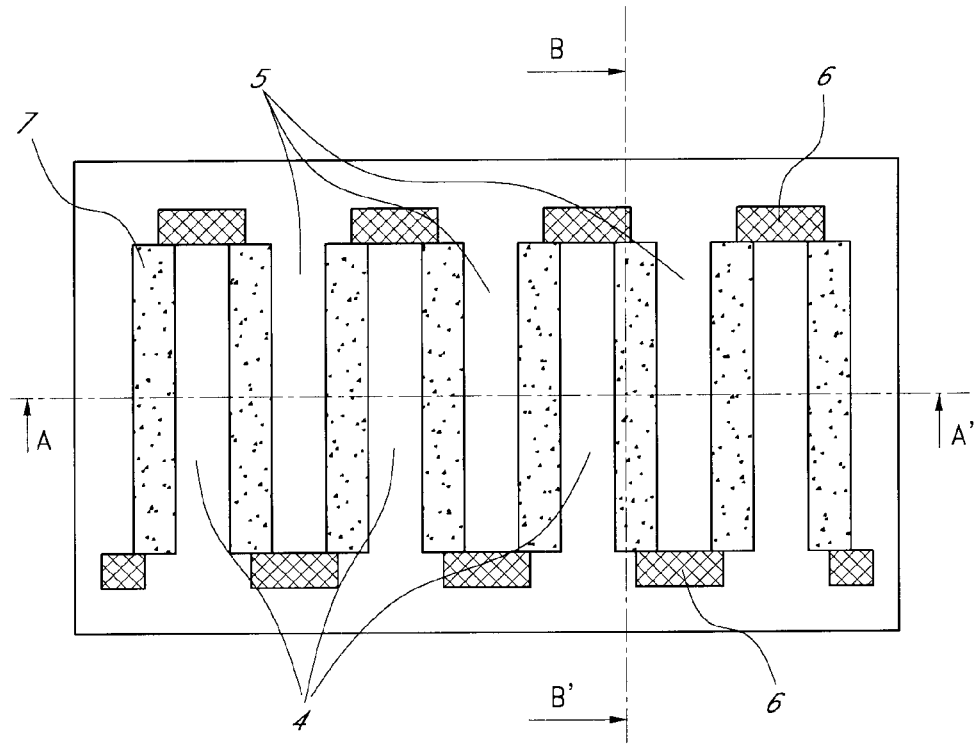
FIGS. 3b, 3c and 3d give a cross-sectional detail of one sensor according to the present invention. (The numbering used is as described for FIG. 2)
Figure 3C:
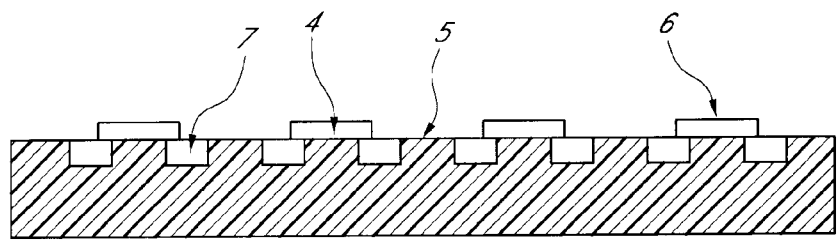
Figure 3D:
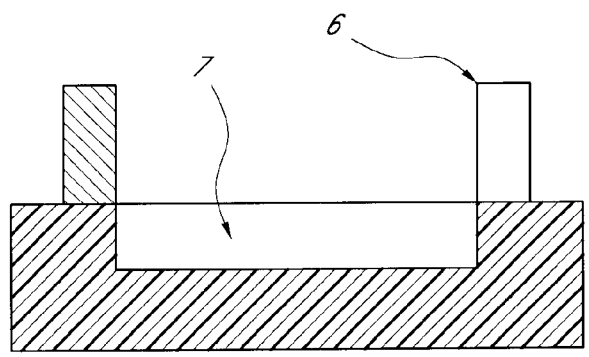

FIG. 2 shows a detailed view of a preferred embodiment of an electronic sensor according to the present invention. This figure shows the active test site area of the sensor in a schematic drawing. This sensor or test site may be fabricated in a sequence of steps as detailed hereunder.

A substrate is to be provided. Said substrate, designating said base layer, can be a cristaline wafer (quartz, silicon, g num), an amorphaus material (glass wafer), a polymer (PMMA, PC, PEEK, PVE, PEI ) or thick film substrate, such as $Al_2O_3$. An insulating layer is formed on said substrate. The insulating layer can be a polymer layer such as polyimide or BCB. The dielectric or insulating layer can as well be $Si_3N_4$ being deposited by LPCVD or PECVD techniques. It can also be a layer of $SiO_2$ that is deposited or thermally grown on said silicon wafer. A specific geometry can then be patterned using known lithography techniques, e.g. photolithography, preferably UV litography, even more preferably deep UV lithography, followed by a selective etching in the $SiO_2$ layer. Another way to produce such insulating structure with a specific geometry is using a moulding process. The reproduction is then done by injection moulding or any other way of making replicates. The mould can then be made with LIGA using X-ray or photolithography, preferably UV litography, more preferably deep UV litography, which allows to achieve very small dimensions. Plastics such as PMMA, PEEK, PVE and PEI can be used as a substrate. The use of these plastics for making microstructures is known in the art.

The moulds fabricated by means of the above-defined methods can be used again as a tool for further replication processes, e.g. as mould inserts for micromoulding or reaction injection moulding. Materials to be used for the replication processes are usually melted polymers and casting resins. After hardening in the metallic form, the mould materials have reached a sufficient strength and the separation of mould and mould insert can take place. For the realization of micromoulding and micro-reaction injection moulding the extremely low roughness of the walls of LIGA fabricated mould inserts is most important.

Materials which have been used for microreplication include low viscosity thermoplastic polymers like polymethyl methacrylate (PMMA), polyoxymethylene (POM), polyamide (PA), or polycarbonate, as well as reaction resins based on methacrylates, silicones and caprolactames. However, many more materials could be used. Except for filled moulding materials, almost any material suitable for macroscopic moulding can be used for micromoulding.

Ceramic microstructures can be fabricated by slurry casting, by using sol-gel processes or by means of electrophoretic and other processes. It is e.g. possible to fill the gaps of a LIGA fabricated polymer structure with a slurry of microcrystalline ceramic powder. After drying and firing, the polymer degrades, evaporates or is oxidized, which results in a ceramic microstructure ("method of the lost form"). The characteristic dimensions of the ceramic structures are smaller than the polymer form, due; to shrinkage during the firing process. Mechanically very stable and temperature persistent materials, piezoelectric materials and ionic conductors can thus be microstructured by means of the LIGA process.

FIG. 3 shows a plate with 2×2 sensors. The chemical composition of this plate can be an insulating on its own or the plate can be composed of a substrate (e.g. a silicon wafer) with an insulating layer (e.g. a $SiO_2$ layer) thereon. The topography of the plate shows pits (7) and hills (6). FIG. 3b gives a detail of one sensor, FIGS. 3c and 3d show cross-sectional views. In a preferred embodiment, the pits (7) are channels (7) having dimensions of the same order of magnitude as the molecules to be detected. Thus the channels are preferably about 100 nm deep and about 100 nm wide, about 100 nm spaced. The spacing in one direction defines adjacent planes (4) (5). The dimensions of the channels can range between about 500 nm deep and about 500 nm wide down to about 10 nm deep and about 10 nm wide, preferably less than 250 nm deep and less than 250 nm wide. This width and deepness may vary independently. The spacing between two channels is of the same order of magnitude as the width and deepness of the channels. The channels are as long as the length of the active test sites area of the bioelectronic sensor. In the sequel, and for the purpose of explaining the invention, this length is assumed to be 0.5 mm Lenghts between 100 µm and 1 mm or smaller or larger are possible. The active area can be made in any geometry, for production purposes by preference a square. It can as well be rectangular. Also the channels can have any shape, e.g. trapezoidal, triangular, rectangular or cylindrical The hills (6) are elevations of a specific height. In this embodiment a height of 1 µm is assumed. The height of the hills can be anything above the width of the channels. Their purpose is to separate the (4) and (5) planes between the channels. The shape of the hills by preference is rectangular but does not necessarily have to be so. The hills are located at the end of the planes (4) (5) between the channels compulsory depassing over the edge of the channel. If at one side of the sensor, they are located at the 'even' planes (4), then they are located at the 'odd' planes at the other side (5) (FIG. 2b). In this embodiment, the hills are about 200 nm long and about 200 nm wide.

Figure 4A:
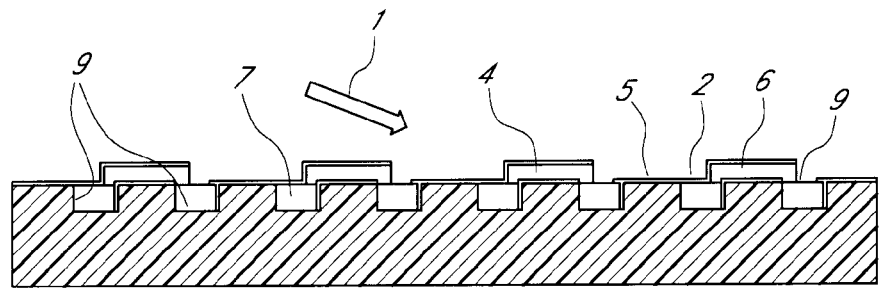
FIGS. 4a, 4b and 4c show schematically a metallization process of the sensor according to the present-invention. (The numbering used is as described for FIG. 2)
Figure 4B:
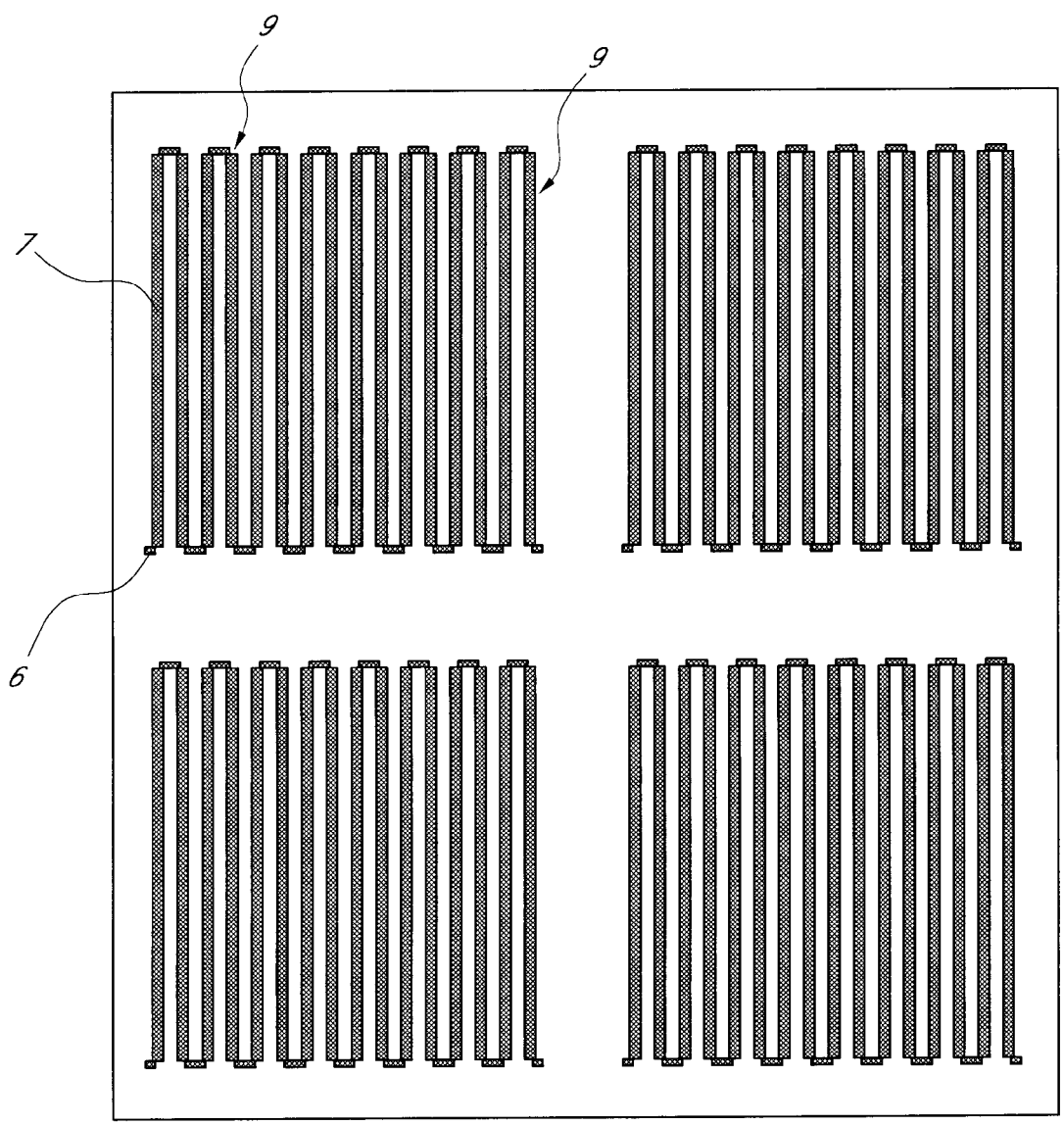
Figure 4C:
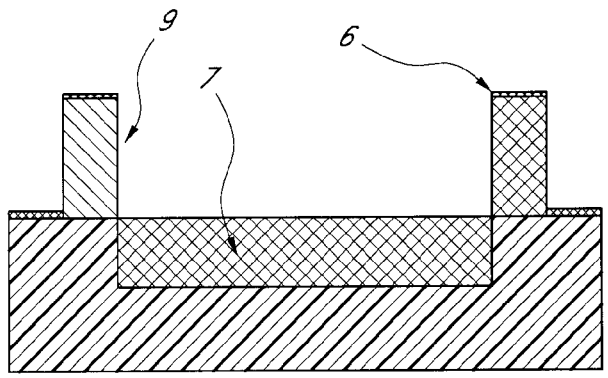

FIG. 4 illustrates the next step in the processing. A metal layer is deposited on the plate under an angle, by preference by means of e-beam evaporation. The direction of the deposition is shown by the big arrow (1). The directionality has to be such that some places (9) on the plate are shadowed and not covered by metal. The angle of metal deposition therefore has to be smaller than 90° as measured with respect to the surface of the plate. By preference the angle of deposition is smaller than 60°, 45° and even smaller than 30°, such as 20°, 10°, 5° or 1°. Said places (9) are at the bottom of the channels and at the side-walls of the channels and of the hills along the deposition direction (1). The planes (4) (5) between the channels are isolated one from another because there is no metal at the bottom of the channels and at the side-walls along the deposition direction (1). Nor are they shortcutted at the edges due to the hills (6) (see FIG. 2 for a 3-D impression). Any metal that does not react with the sample solution can be used. Examples are Pt, Pd, Au or less noble metals like Ag or Al provided that chemical reactions at the electrodes are expelled. The thickness of the metal layer or metal coating can range inbetween about 2 nm, 50 nm, 100 nm, 200 nm or thicker, preferably the metal thickness is 20 nm. The metal deposition can be achieved using thermal evaporation, sputtering, e-beam deposition or any other technique known for depositing metals such as an impinging flux of metals.

Figure 5A:
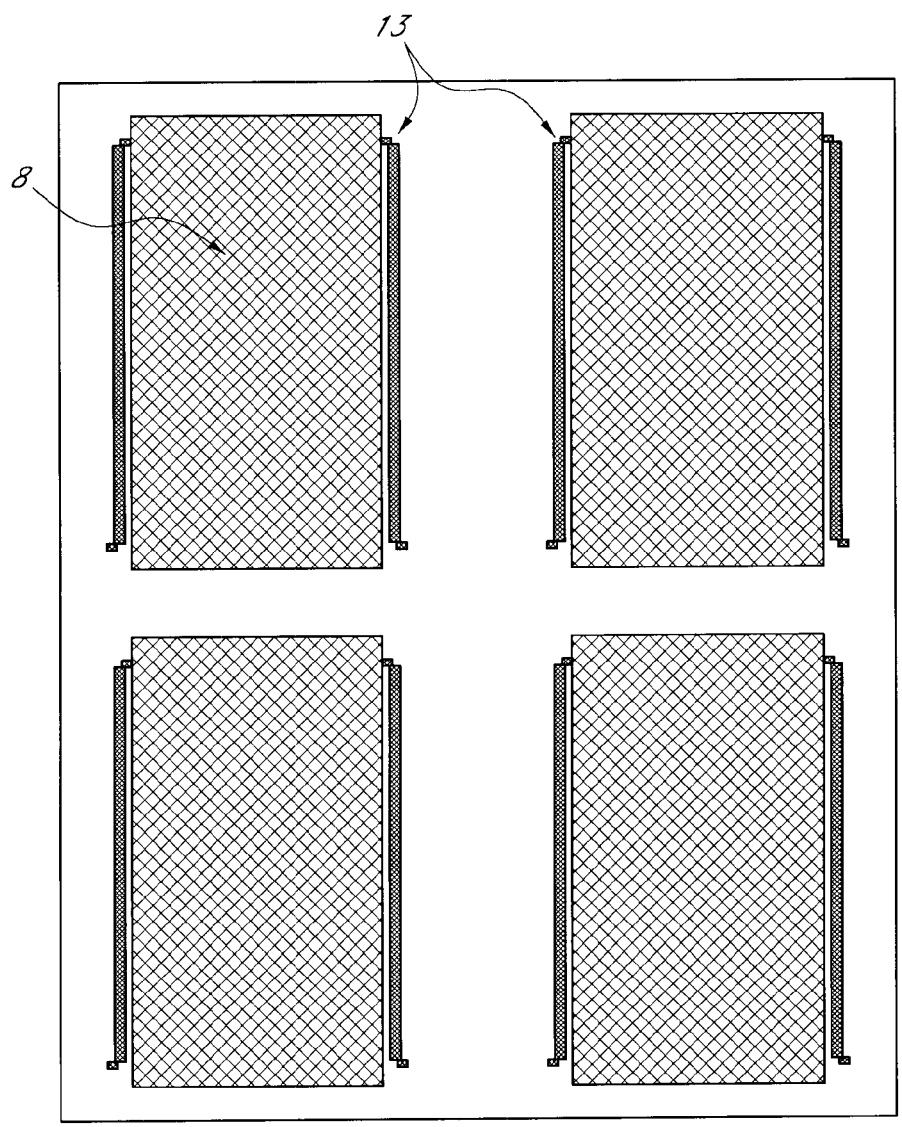
FIG. 5a illustrates how a shadow mask is applied for achieving a final structure.
Figure 5B:
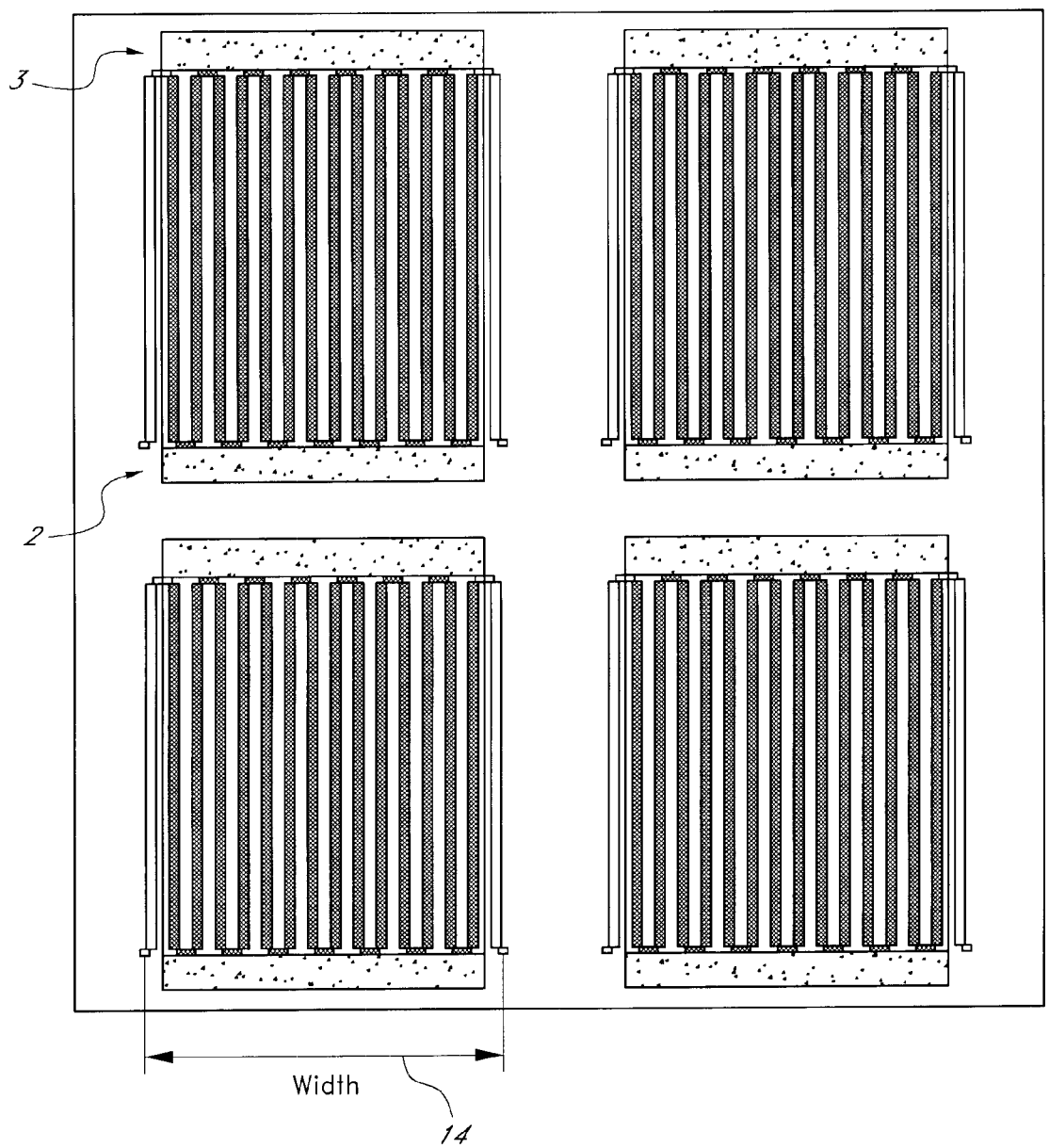
FIG. 5b shows the sensor array after etching through this mask. (The numbering used is as described for FIG. 2)

The different sensors in an array (in this example 2×2 sensors) are however still shortcutted. Selective etching of the evaporated metal separates the different sensors. FIG. 5a shows the application of a mask (8). This mask can be lithographically transferred to a resist pattern, or it can be a shadow mask. If the structure is etched like this, the structures under the masking layer remain and the non-covered area is etched. FIG. 5b shows the result of this etching in separated sensors. These separated sensors can be a possible final structure. These separated sensors with probes attached thereon are also a possible final structure. Separated bonding pads (2) and (3) are achieved and thus an interdigitated electrode structure results.

The shaded area of the mask (8) in FIG. 5a determines the active array of the sensor and the positive (2) and negative bonding pads (3) The open area of the mask is etched away (cf. above) and separates the different sensors from each other. The alignment of the mask (8) is not critical. An alignment accuracy of 10 µm is sufficient for this embodiment. The up and down sides in FIG. 5a are defining the bonding pads (2) and (3) and their final dimension is not critical. The dimensions of the left and right sides on FIG. 5a are not critical neither. The mask (8) is namely 50 µm smaller than the width (14) of all the channels. The final active area is thus determined by mask (8). Some fingers (13) are sacrificed and etched away. This means that a misalignment of half this width of 50 µm (i.e. 25 µm) does not have any influence, because the active area is still filly covered with channels (7) and the resulting finger electrodes (4) and (5), being the metallized planes. This procedure prevents from needing structuring methods with a sub-micron resolution.

Other methods known in the art to separate the different sensors may also be used within the scope of the present invention.

Figure 6A:
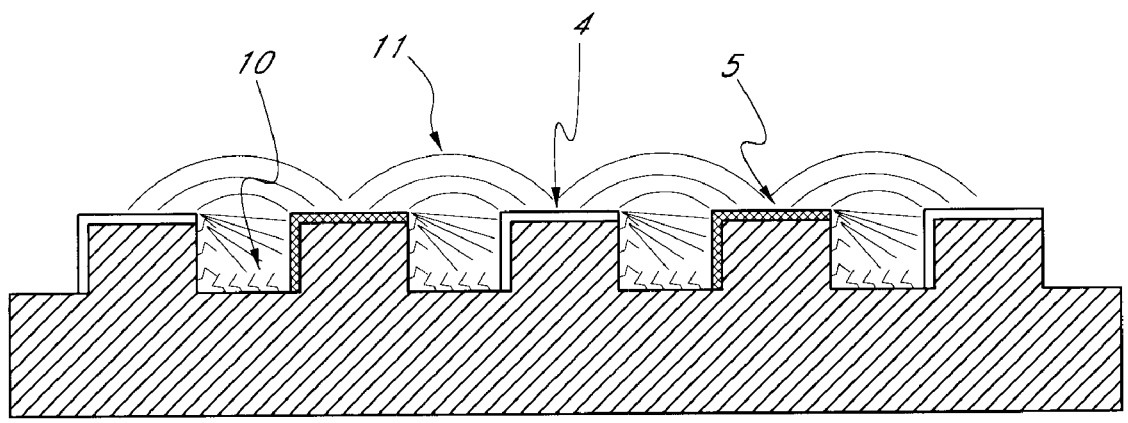
FIG. 6a shows a sensor without 'recognized' molecules.
Figure 6B:
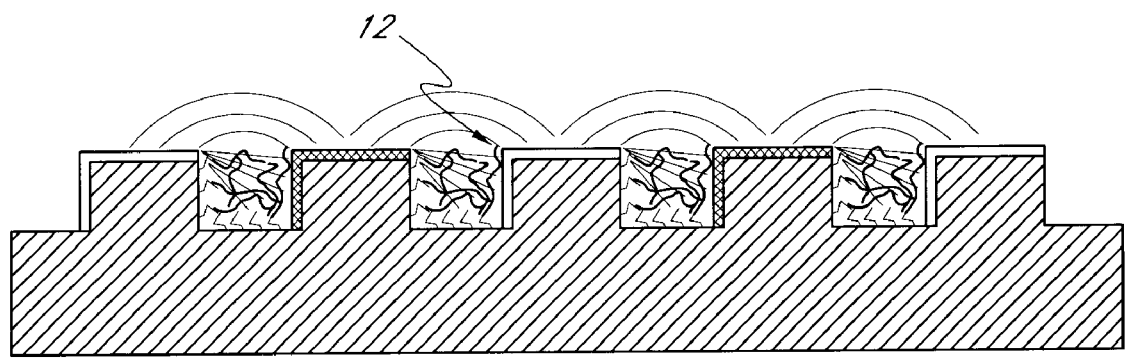
FIG. 6b with 'recognized' molecules. (The numbering used is as described for FIG. 2)

FIG. 6 shows one possible way of the the working principle of a sensor of the present invention. Probes (10) may be immobilised in the insulating areas of the channels according to probe immobilization methods known in the art as such epoxy linkage, carbodiimide, reductive amination, cyanogen bromide, succinimide, carbodiimidazole, tresyl and tosyl chloride, divinyl chloride, maleimide, hydrazide, iso(thio)cynates and more preferred silanization with amino sianes, epoxysilanes, thiocyanato silanes, isocyanato silanes, succinic anhydride silanes, sulihydryl slanes, caprolactam silanes and so on. However, in other measurement configurations and/or set-ups, the probes can be selectively immobilised:

only on metallic surfaces, for example by adsorption of sulfur containing moieties at a Au layer, or all over the active test site area: on the insulating and the conductive layers, for example by a sequential immobilisation process or by plasma polymerisation of an organic layer exhibiting reactive groups, like amino, sulfhydril, aldehydes, carboxyl, hydroxyl and so on.

The probes in the context of the present invention may be, by way of example and not by way of limitation, enzymes (with affinity for specific substrates), oligonucleotides (with affinity for specific DNA and RNA fragments), antibodies (with affinity for specific antigens), antigens (with affinity for specific antibodies), or any other component of a analyte/coanalyte complex.

By applying an electrical signal, i.e. voltage or current, on the bonding pad (3) and bonding pad (2) (FIG. 2) an electric field arises, resulting in electric field lines (11). If the analyte to be detected (12) is in a sample solution it will bound to the specific probes (FIG. 6b), resulting in a change in the electric field (11) in contrast with the situation depicted in FIG. (6a). This change can be quantitated by measuring the impedance at the proper frequency and/or dc bias. By preference this electrical measurement is an impedance analysis, which can devolve in a measurement of resistance, capacitance, dielectric loss and/or reactance over a frequency range, including or not dc bias, or a combination of these techniques.

Due to the sub-micron dimensions of the channels and due to the shape of the electrodes (emerging from the deposition of metal under an angle), the electric fields (11) strongly penetrate in the region with the immobilised probes (11). An even stronger confinement of the electrical fields in the region of interest would be achieved in case when a second insulating layer is put on top of the (4) and (5) planes. In this way the electrical field lines probe more the interior of the channels where the bound analyte occupies most of the space.

Figure 7A:
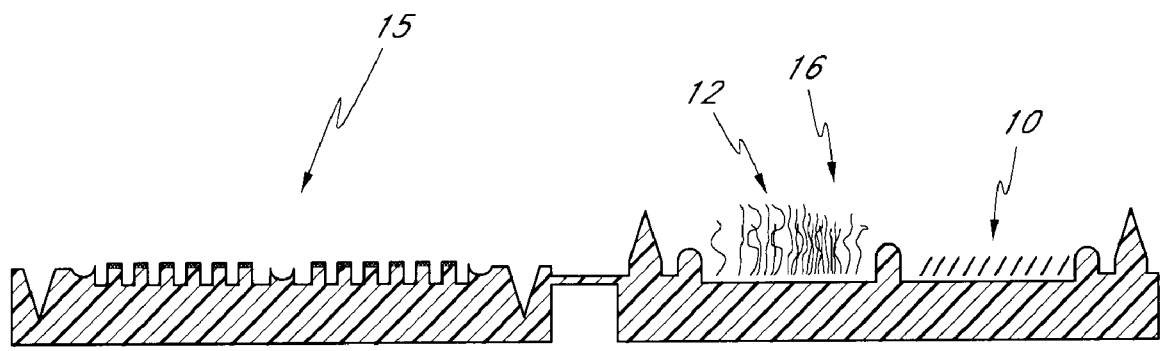
FIGS. 7a and 7b show a specific embodiment of the bioelectronic sensor of te present invention. (The numbering used is as described for FIG. 2)
Figure 7B:
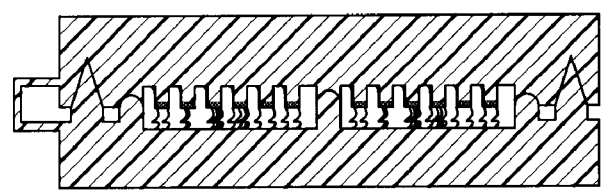

When fabricating a sensor according to the present invention with the smaller dimensions (sub 100 nm) larger molecules that have to be detected might not enter the channels anymore due to steric hindrance. FIG. 7 shows schematically how this problem can be overcome. A sensor is to be fabricated that can be split in two. The left side (15) of the sensor consists of an array of sensors with the interdigitated electrode structure, fabricated in the same way as discussed above. The right hand side (16) is covered with immobilized probes (10) in such a way that they will correspond with the array of sensors once they are brought in contact with each other by pleating the structure. The sample solution comprising the molecular structures and elements that are to be detected is put (incubated) on top of the right hand side (16). Certain molecules (12) will bind to the probes (10). After this recognition process, the sensor is closed by folding (FIG. 7b). The application of mechanical force brings the probes (10) and molecules (12) close enough to the interdigitated electrode structure, so that eventually a difference in impedance of the incubated versus a not incubated structure can be measured.

The present invention describes sensors which are suitable for real time measurements, i.e. the binding process during different incubation steps, with or without different condition changes, like for instance temperature.

The present invention also allows very flexible measurement set-ups such as analyte immobilisation on the surface of the sensing device and recognition of certain probes applied in the solution phase.

The described technological process and the high sensor miniaturisation also allow the construction of microdiagnostic devices.

Sensor arrays comprising different probes can be fabricated in the way just described, to result in microdiagnostic devices. Said integrated microdiagnostic devices are capable of simultaneous detection of a multitude of parameters, i.e. multiparameter testing. This is of particular importance for limited sample situations like in the case of neo-natals blood samples, for reliable diagnosis requirements like in the case of transplantation immnology, autoimune diseases or blood-infections and ultimately for screening assays.

Such juxtaposed microdiagnostic arrays have the additional advantage that they can process parallely and simultaneously several different samples.

What is claimed is:

1. A sensor comprising:
    an insulating layer with a self-contained shadowing property, said layer comprising a top and a plurality of interspaced channels having the same direction, each of said channels having a bottom and two opposite sidewalls;
    a metal coating applied on at least part of one of said two opposite side-walls of each channel and on at least part of the top of the insulating layer in-between said channels, thereby forming part of an impedimetric device comprising two electrodes which are interdigitated as a result of the shadowing property; and
    a plurality of hills located on at least one end of the plane formed between said channels, said hills producing the self-contained shadowing property of the sensor.

2. A sensor according to claim 1, where said hills have a height which is larger than the width of the channels, and said hills overlap the plane between said channels and part of two adjacent channels.

3. A sensor according to claim 1, further comprising probes for binding to target molecules present in a sample to be tested, said probes being immobilized on either the insulating part of the channels and/or on the surface of the electrodes.

4. A sensor according to claim 1, wherein said insulating layer is applied on a base layer substrate.

5. A sensor according to claim 4 wherein said substrate is a silicon wafer.

6. A sensor according to claim 1, wherein the width of said channels are within a range of 10 nm to 500 nm.

7. A sensor according to claim 6 wherein said channels are 100 nm deep and 100 nm wide, said channels being interspaced by 100 nm.

8. A sensor according to claim 1, wherein said insulating layer is a thermal $SiO_2$.

9. A sensor according to claim 1, wherein said insulating layer is a polymer.

10. A method of producing a sensor, said method comprising the steps of:
    forming a plurality of interspaced channels in an insulating layer, said channels having the same direction, each channel of said channels having a bottom and two opposite side walls and hills, said hills being located at the end(s) of planes between said channels, having a height which is larger than the width of the channels, and overlapping the plane between said channels and part of two adjacent channels;
    depositing a metal layer on said insulating layer while aligning said insulating layer with respect to a metal deposition source such that the bottom of said channels and the side-walls of said channels along deposition direction are shielded and not covered by metal to thereby form and impedance comprising electrodes; and
    optionally applying probes for binding to molecular structures present in a sample to be tested, and said probes being immobilized on either the insulating part of the channels and/or on the surface of the electrodes.

11. A method according to claim 10 wherein the metal layer is deposited at an angle of smaller than 90° with respect to said insulating layer.

12. A method according to claim 10 further comprising the step of applying said insulating layer on a base layer substrate.

13. A method according to claim 10, wherein said substrate is a silicon wafer and said insulating layer is thermal $SiO_2$.

14. A method according to claim 10, wherein the step of forming said channels is executed using microelectronics patterning techniques.

15. A method according to claim 14 wherein the step of forming said channels is executed by a photolithographic process.

16. A method according to claim 10, wherein said insulating layer is a polymer.

17. A method according to claim 16 wherein said polymer is structured by microstructure molding.

18. A sensor apparatus for identifying molecular structures within a sample solution, comprising:
    a plurality of sensors, wherein said sensor comprises:
    an insulating layer with a plurality of interspaced channels therein having the same direction, each channel of said channels having a bottom and two opposite side-walls and hills, said hills being located at the end(s) of planes between said channels, having a height which is larger than the width of the channels, and overlapping the plane between said channels and part of two adjacent channels;
    a metal coating being applied on at least part of one of said two opposite side walls of each channel and on at least part of the top of the insulating layer in-between said channels thereby forming part of an impedimetric device comprising 2 electrodes;
    optionally an additional insulating layer applied above said sensor in order to confine the electrical field in said channel between the two separated parts of said metal coating;

apparatus for applying a voltage on the metal coatings; and apparatus for measuring the electrical properties or the impedance in-between the electrodes of the sensors to determine which probes have bonded to their target molecule(s).

19. A sensor apparatus according to claim 18 further comprising a connector to said metal coatings, said connector bonding the active area of said sensor and being oriented perpendicular with respect to said direction and said voltage being applied on said connector.

20. An array of sensors, said array being a geometric configuration of the sensors, wherein said sensor comprises:

an insulating layer with a plurality of interspaced channels therein having the same direction, each channel of said channels having a bottom and two opposite side-walls and hills, said hills being located at the end(s) of planes between said channels, having a height which is larger than the width of the channels, and overlapping the plane between said channels and part of two adjacent channels;

a metal coating being applied on at least part of one of said two opposite side walls of each channel and on at least part of the top of the insulating layer in-between said channels thereby forming part of an impedimetric device comprising 2 electrodes;

the different sensors of the array being parallel to one another.

21. A method for identifying molecular structures within a sample solution comprising the steps of:

applying said sample solution to a plurality of sensors, each sensor having one or more probes applied therein to bond with an associated target molecular structure, and each sensor comprising:

an insulating layer with a plurality of interspaced channels therein having the same direction, each channel of said channels having a bottom and two opposite side-walls and hills, said hills being located at the end(s) of planes between said channels, having a height which is larger than the width of the channels, and overlapping the plane between said channels and part of two adjacent channels;

a metal coating being applied on at least part of one of said two opposite side walls of each channel and on at least part of the top of the insulating layer in-between said channels thereby forming part of an impedimetric device comprising 2 electrodes;

applying an electronic signal to the sensor; and measuring the electrical properties of the sensor to determine which probes have bonded to their target molecular structure(s) such that a plurality of different targets can be detected.

22. A method according to claim 21 wherein said sensor has one or more types of oligonucleotide probes applied therein.

23. A method according to claim 21 wherein said sensor has one or more types of antibody probes applied therein.

24. A method according to claim 21 wherein said sensor has one or more types of antigen probes applied therein.

25. A method according to claim 21 wherein said sensor has one or more types of peptide probes applied therein.

26. A method according to claim 21, wherein said probe (s) is (are) covalently or non-covalently attached to said sensor.

27. A sensor apparatus according to claim 18, further comprising one or more types of probes applied to said sensors at either the insulating part of the channels and/or to the surface of the electrodes for bonding with an associated target molecular structure.

28. A sensor assembly comprising:

a first part comprising an array of sensors, said array being a geometric configuration of the sensors, wherein said sensor comprises:

an insulating layer with a plurality of interspaced channels therein having the same direction, each channel of said channels having a bottom and two opposite side-walls and hills, said hills being located at the end(s) of planes between said channels, having a height which is larger than the width of the channels, and overlapping the plane between said channels and part of two adjacent channels;

a metal coating being applied on at least part of one of said two opposite side walls of each channel and on at least part of the top of the insulating layer in-between said channels thereby forming part of an impedimetric device comprising 2 electrodes;

wherein the different sensors of the array being parallel to one another;

a second part comprising an array of containers to which probes are attached; and with said first and said second parts being brought into contact in such a way that said array of containers corresponds to said array of sensors.

29. A sensor according to claim 2, further comprising probes for binding to molecular structures present in a sample to be tested, said probes being applied to either the insulating part of the channels and/or to the surface of the electrodes.

30. A sensor according to claim 29, wherein the dimensions of said channels are within a range of 10 nm to 500 nm.

31. A sensor according to claim 30 wherein said channels are 100 nm deep and 100 nm wide, said channels being interspaced by 100 nm.

32. A sensor apparatus according to claim 18, wherein said insulating layer comprises a polymer.

33. An array of sensors according to claim 20, wherein said insulating layer comprises a polymer.

34. A method according to claim 21, wherein said insulating layer comprises a polymer.

35. A method for identifying molecular structures within a sample solution comprising the steps of:

applying said sample solution to a plurality of sensors, said plurality of sensors forming an array, said array being a geometric configuration of the sensors, wherein each sensor has one or more probes applied therein to bond with their target molecular structure and comprises:

an insulating layer, with a plurality of interspaced channels therein having the same direction, each channel of said channels having a bottom and two opposite side-walls and hills, said hills being located at the end(s) of planes between said channels, having a height which is larger than the width of the channels, and overlapping the plane between said channels and part of two adjacent channels;

a metal coating being applied on at least part of one of said two opposite side-walls of each channel and on at least part of the top of the insulating layer in between said channels thereby forming part of an impedimetric device comprising 2 electrodes;

the different sensors of the array being substantially parallel to one another along said direction;

applying an electronic signal to the sensor; and measuring the electrical properties of the sensor to determine which probes have bonded to their target molecular structure(s) such that a plurality of different targets can be detected.

36. A method for identifying molecular structures within a sample solution comprising the steps of:

applying said sample solution to a plurality of sensors, each sensor having one or more probes applied therein to bond with their target molecular structure and obtainable by a method comprising the steps of:

forming a plurality of interspaced channels in an insulating layer, said channels having the same direction, each channel of said channels having a bottom and two opposite side-walls and hills, said hills being located at the end(s) of planes between said channels, having a height which is larger than the width of the channels, and overlapping the plane between said channels and part of two adjacent channels;

depositing a metal layer on said insulating layer while aligning said insulating layer with respect to a metal deposition source such that the bottom of said channels and the side-walls of said channels along deposition direction are shielded and not covered by metal to thereby form an impedance comprising electrodes; and optionally applying probes for binding to molecular structures present in a sample to be tested, said probes being immobilized on either the insulating part of the channels and/or on the surface of the electrodes;

applying an electronic signal to the sensor; and measuring the electrical properties of the sensor to determine which probes have bonded to their target molecular structure(s) such that a plurality of different targets can be detected, wherein said sensor has one or more types of probes selected from the group consisting of oligonucleotide probes, antibody probes, antigen probes, and peptide probes applied therein.

37. A method according to claim 35, wherein said sensor has one or more types of probes selected from the group consisting of oligonucleotide probes, antibody probes, antigen probes, and peptide probes applied therein.

38. A method according to claim 36, wherein said probe(s) is covalently or non-covalently attached to said sensor.

39. A method according to claim 37, wherein said probe(s) is covalently or non-covalently attached to said sensor.

40. A sensor according to claim 1, wherein said insulating layer comprises a polymer.

* * * * *